United States Patent [19]

Kearns et al.

[11] Patent Number: 5,074,942
[45] Date of Patent: Dec. 24, 1991

[54] METHOD FOR MAKING INTRAOCULAR LENS WITH INTEGRAL COLORED HAPTICS

[75] Inventors: William J. Kearns, Costa Mesa; Henry Orlosky, Irvine, both of Calif.

[73] Assignee: Texceed Corporation, Costa Mesa, Calif.

[21] Appl. No.: 523,371

[22] Filed: May 15, 1990

[51] Int. Cl.$^5$ .................. B32B 31/00; B29C 65/00; A61F 2/16
[52] U.S. Cl. .................... 156/154; 156/250; 156/304.2; 156/305; 623/6; 623/901
[58] Field of Search .............. 623/6, 901; 156/294, 156/304.2, 154, 156, 250, 305; 264/1.7

[56] References Cited

U.S. PATENT DOCUMENTS

| 4,676,791 | 6/1987 | LeMaster et al. | 623/6 |
| 4,813,956 | 3/1989 | Gupta | 623/6 |
| 4,834,749 | 5/1989 | Orlosky | 623/6 |
| 4,923,466 | 5/1990 | Pintucci | 156/305 X |
| 4,961,746 | 10/1990 | Lim et al. | 623/6 |

FOREIGN PATENT DOCUMENTS 2181355A 4/1987 United Kingdom .................... 623/6

Primary Examiner—Ronald Frinks
Attorney, Agent, or Firm—Lyon & Lyon

[57] ABSTRACT

An improved method for making a monolithic intraocular lens and haptic structure. The invention comprises the process of assembling easily available materials into a composite structure having an inner core of optically transparent lens material with broad or selectively tailored wavelength transmission characteristics surrounded by a jacket of colored haptic material having the same composition and mechanical properties as the lens material. The composite structure is then bonded into a monolithic rod with a bonding process wherein the bonding material in the interface between the lens core and the jacket also has the composition and mechanical properties of the lens material. After bonding, the composite structure is sliced into blanks from which lenses with colored haptics can be fabricated.

11 Claims, 2 Drawing Sheets

METHOD FOR MAKING INTRAOCULAR LENS WITH INTEGRAL COLORED HAPTICS

BACKGROUND OF THE INVENTION

This invention relates to an improved method for making an intraoclular lens with integral colored haptics. Haptics are springy, filamentary lens supports, at least two in number, located about and attached to the periphery of an intraocular lens for the purpose of centering and holding the lens in proper position in the eye. At present, there are two intraocular lens-haptic structures in common use, the monolithic lens-haptic structure and the composite lens-haptic structure. The first type is a monolithic structure in which the haptics or other analogous support means are fabricated directly from a thin annulus around the lens which is an integral part of the lens itself. A lens of this type is shown in FIGS. 1A and 1B. The second lens-haptic structure is a composite unit comprising a lens with at least two filamentary haptics attached to the lens by a fastening process. An example of this type of lens is shown in FIGS. 2A and 2B.

A disadvantage of existing monolithic lens-haptic structures is that they have uncolored haptics since the haptics are made from the same material as the lens. The uncolored, transparent haptics are difficult to see; thus, the implantation of the intraocular lens is sometimes an unnecessarily prolonged and difficult process. Also, the thin haptics occasionally break off during surgery or must be explanted subsequent to disease or trauma. Because they are highly transparent, broken haptics which must be retrieved from the eye are extremely difficult for a surgeon to see. Leaving a broken haptic in the eye could produce serious negative effects for the patient. Attempts to color the integral haptics have met with limited success since any coloring material must be biologically inert with respect to the eye, and there are few such materials. Applying a surface coloration to the integral haptics has not been successful because the colored layer may lose adherence to the haptics and peel off. A haptic is only about five thousandths of an inch thick (about 0.1 mm), so such a colored layer must be quite thin. If the colorant is a dye which permeates the haptic by diffusion, the dye material could diffuse out of the haptic into the eye, and the mechanical properties of the haptic could be undesirably altered in the coloring process. Thus, the main barrier to fabricating a monolithic lens is the difficulty in making the integral haptics visible. Jaffe, U.S. Pat. No. 4,822,358, Anis, U.S. Pat. No. 4,878,911. and Hetland, U.S. Pat. No. 4,778,463 show several of these types of integral haptic configurations without any coloration of the haptic material.

Composite lens-haptic structures have widespread use because of the availability of biocompatible colored or opaque filamentary material for the haptics. The haptic material can be colored thermoplastic or thermoset filaments, or metal wires. All of these types of haptics are easily visible to a surgeon should one become separated from the lens during the implantation process. With the separately fabricated filamentary haptics, the colorant does not diffuse into the eye from the haptics. Haptics of this type are described in Orlosky, U.S. Pat. No. 4,834,749, and in Knolle, U.S. Pat. No. 4,588,405. Another advantage of the filamentary haptic is that it is usually stronger and more resistant to damage during surgery than the haptics machined from the lens material as in monolithic lenses. Even though this second type of haptic is in widespread use, some surgeons prefer the one-piece lens with integral haptics, especially if the haptics could safely be made more visible in the eye or more resistant to damage during surgery. Manufacturers of intraocular lenses also prefer a monolithic lens-haptic structure because the manufacturing yields are thought to be better for this mode of fabrication.

Therefore, an object of this invention is to produce an improved method for making a monolithic lens-haptic structure with integral colored haptics which are visible to the surgeon implanting a lens.

Another object of this invention is to produce an improved method for making a monolithic lens-haptic structure having integral colored haptics that are as strong as the haptics in the existing one piece intraocular structures with clear haptics.

An additional object of this invention is to produce an improved method for making a monolithic lens-haptic structure with integral colored haptics in which the colorant of the haptics will not transfer from the haptics to the inner structure of the eye.

A further object of this invention is to produce an improved method for making haptics that are less likely to break either during or after the implantation process than haptics made of lens material.

Still another object of this invention is to produce an improved method for making a lens-haptic structure with integral colored haptics in an economically feasible way.

SUMMARY OF THE INVENTION

The present invention relates to an improved method for making a monolithic intraocular lens-haptic structure. An exemplary embodiment of the invention comprises the process of fabricating an inner core of optically transparent lens material, fabricating segments of an annulus of colored haptic material having the same composition and the same or superior mechanical properties as the lens material, and bonding the inner core and segments into a composite structure that becomes a monolithic rod. The bonding process produces an interface between the lens core and the annular colored haptic material which has the same composition or and mechanical properties of the lens material. The bond is, in effect, a weld in which the interface between the lens and the haptic is the same material as the lens and haptic. Thus a cross section through any interface between the inner lens material and the outer haptic material reveals no change in compositional characteristics; only the optical properties, i.e., color or refractive index, and in some cases improved strength and fracture resistance, vary from component to component. A suitable bonding process can be chosen from various methods known to those skilled in the art. The invention allows the freedom to use haptic material of one or more contrasting colors, combined with lens material having broad or selectively tailored wavelength transmission, and/or radially variable refractive index. In this way a monolithic, multi-colored rod results. Slices of lens and haptic material can be cut from this rod to form blanks from which the one-piece lens-haptic structures can be made. The blanks are then machined to produce the clear lens with integral colored haptics.

DESCRIPTION OF THE PREFERRED EMBODIMENT

Figure 1A:
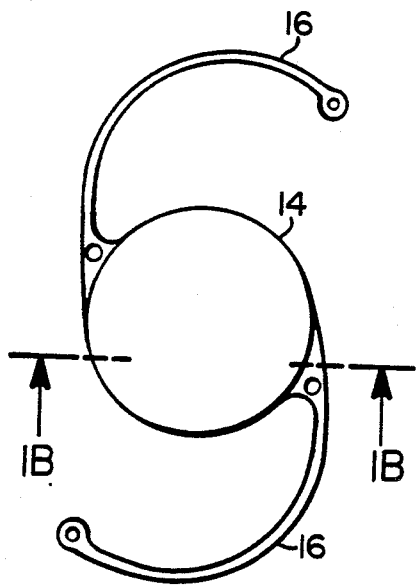
FIG. 1A is a plan view of a one-piece intraocular lens of the prior art showing two integral haptics.

Monolithic intraocular lenses made by forming the lens and supporting structures from one piece of lens material are a desirable type of lens and the choice of many ophthalmologists. However, since the haptics are formed from the same material as the lens, they are transparent and therefore difficult for the surgeon to see during the implantation operation. Since most intraocular lenses are made of poly(methyl methacrylate) (PMMA), the logical choice of haptic material is also PMMA. Attempts to alter the optical properties of the transparent haptic portion of the monolithic intraocular lens to increase the optical contrast between the haptics and tissues of the eye have been unsuccessful. Since the haptics are machined from the same blank as the transparent lens, they must be coated or dyed after fabrication to increase the optical contrast. Coatings can separate from the slender haptic surface and allow undesirable particulate matter to be loose in the eye which can cause serious complications for the patient. To add color, the haptics can be dyed after the lens assembly is machined. In the dyeing process, the haptic material absorbs the dye which diffuses inwardly into the body of the haptic. As a result of the diffusion process, several difficulties occur. For example, once a lens with a dyed haptic is in place in the eye, the diffusion process may continue so that the dye could move into the body of the lens at the juncture of the haptic and the lens, causing clouding of the lens at that point. Also, the diffusion process by which the dye material colors the haptic may reverse itself, and the colorant may diffuse outwardly from the haptic into the tissues and fluids of the eye. Thus a foreign material could be introduced into the interior of the eye after implantation.

Both of the above situations are intolerable to the patient and to the long-term success of the implant. Furthermore, depending upon the process used to color the haptic, the introduction of chemical additives into the fabricated haptic may have deleterious effects on the mechanical and chemical properties of the haptic, complicating the implantation process or producing negative effects for the patient. To preclude these objectionable potentialities, the coloring or opacifying agent should be so securely bound to the haptic material that it cannot delaminate or diffuse out of the haptic proper.

One way to fabricate such a lens structure, according to existing technology and taught in Gupta, U.S. Pat. No. 4,813,956, is to drill an array of holes in a sheet of opaque or deeply colored PMMA material that has physical and chemical properties similar to the lens. The holes are then filled with clear plugs of PMMA lens material which are securely cemented into place. Circular two-colored blanks are then cut from this sheet, each blank being symmetrically located about the center line of the clear plug. These two-colored blanks are then machined into a lens structure which has opaque or colored haptics, thus forming a monolithic lens structure.

Figure 3:
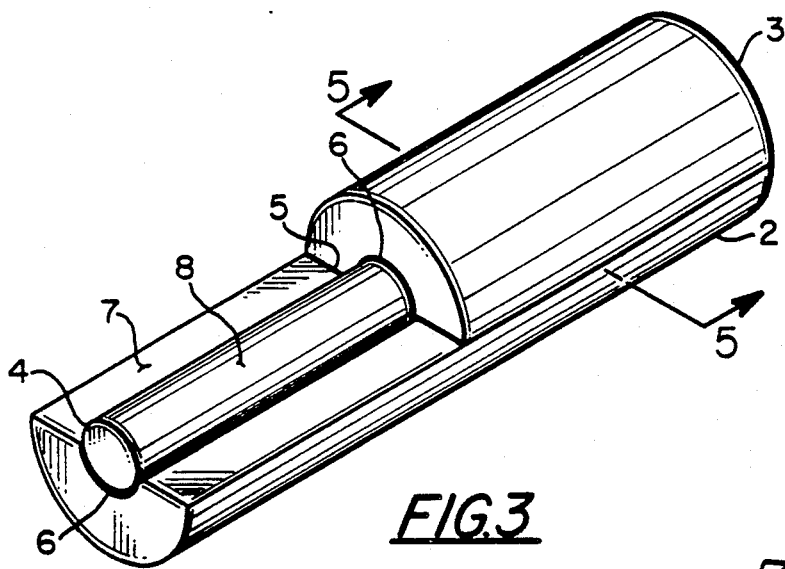
FIG. 3 is an isometric view showing the configuration of the composite rod structure for making monolithic intraocular lenses.
Figure 4:
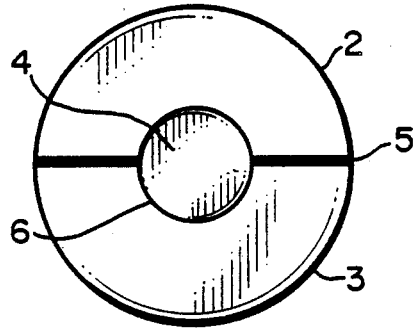
FIG. 4 is a plan view of a slice from the composite rod structure which is a blank from which a lens can be machined.

The improvement according to this invention, is in the method for making such blanks from which lenses are machined. The method results in low manufacturing costs and high yields. The composite rod assembly shown generally as 1 in FIG. 3 is the feedstock from which two-color blanks are made. These composite rods are of arbitrary length, depending on what is most convenient for forming and handling the parts. In the preferred embodiment, the central rod of lens material is encapsulated by a colored annulus of circular cross section; however, non-circular cross-sectional shapes may be utilized if desired or necessary, as would be apparent to those skilled in the art. For ease of discussion, circular cross-sectional geometry is assumed; however, the following remarks apply equally to non-circular cross sections.

The colored annulus comprises two nominally identical annular segments 2 and 3 of 180 degrees subtended angle. These annular segments surround the center core 4 of clear lens material and are securely bonded thereto. The key feature of this invention is that, by forming all the parts of the composite rod separately, the sealing surfaces 7 and 8 are available for the uniform application of a bonding material prior to assembly. This uniform application of the bonding material in the manner of this invention thus ensures the uniformity and integrity of the bond between components and does so in an economically feasible way.

To further ensure uniformity and integrity of the bond between components, the spacings 5 between the two colored annular segments and the spacing 6 between the core material and the colored annular segments are carefully controlled through the use of positioning jigs or fixtures. After assembly, the spaces are a nominal four thousandths of an inch (about 0.1 mm) with a tolerance of plus or minus 25%. After the bonding process is complete, the rod is cut into wafers or blanks of proper thickness for machining lenses.

The colored annular segments can be made in a variety of ways. In the preferred embodiment the segments are molded, cast or extruded, and the clear lens core is molded or cast. These methods are chosen as inexpensive processes for forming the required shapes with suitable optical and mechanical properties. However, as would be apparent to one skilled in the art, any of the parts can be made by a variety of processes such as extruding, molding, casting, or machining from the raw material. The preferred embodiment utilizes two 180 degree annular sectors for total encapsulation of the lens core material; however, it is possible to construct the annulus so it has three or more encapsulating pieces. For example, three nominally identical 120 degree annular segments could form a complete annulus. Utilizing annular segments of the same cross-sectional shape to form the annulus is desirable for minimum cost of fabrication, but various shapes for special applications are well within the scope of this invention. Although, in the preferred embodiment, the annulus for the haptic material completely surrounds the lens core, the method of this invention is amenable to the assembly of spaced segments if cost or subsequent lens fabrication techniques require such a geometry for the monolithic rod. The method of this invention is also well suited for making monolithic rods of more than one color in any one encapsulating assembly if, for example, it is necessary or desirable for color coding, assuming various colorants that are biologically compatible with the eye are available.

Additional improvement in the mechanical properties of the PMMA haptics may be obtained by using material that has been stretched in two mutually perpendicularly directions. The stretching process aligns the molecular structure of the PMMA resulting in greatly increased resistance to fracture and crazing. The chemical and solvent bonding characteristics, however, are unchanged so that the bonding process described above applies in the same way to the stretched material. Thus, lens-haptic structures made from such material may approach the mechanical properties of filamentary lens-haptic structures but have the advantages of monolithic form.

Variations on the configuration of the colored annulus portion of the monolithic rod assembly have been disclosed. Similarly, there are a number of features of the lens core material which are within the scope of this invention. One such variation is the inclusion of radiation-blocking formulations for the clear lens material, especially for reducing ultraviolet transmission. Another variation is the modification of the index of refraction of the lens core in the radial direction, resulting in a gradient refractive index lens for special vision correction needs. The lens core material may be other than optically passive material, i.e., its optical properties vary with the intensity of incident light. Such material would come from a class of optically active materials which include photochromic and other optically non-linear materials for control of light transmission. For example, a photochromic material would augment the light-attenuating action of the iris, providing a therapeutic effect in patients with compromised iris function or photophobia. Other non-linear optical materials to restrict transmission of potentially eye-damaging, intense bursts of light can be utilized. Such lens formulations would be of value to patients exposed to laser light, welding arcs, or nuclear detonations.

Either during or after fabrication of the lens core and the two annular segments in the preferred embodiment, the surfaces to be bonded, 7 and 8, are given a rough surface texture, not unlike a sandblasted finish, to facilitate the bonding process. A uniform surface texture with a roughness of three to six micrometers (125 to 250 microinches) is representative. In the preferred embodiment the chordal planes of the annular segments are ground lightly to impart the rough surface specified above and to ensure planarity of the mating surfaces. Similarly, the central core rod is centerless ground to produce a cylindrical surface with the properly roughened finish. Thus the tolerances mentioned above can be easily achieved.

Figure 5:
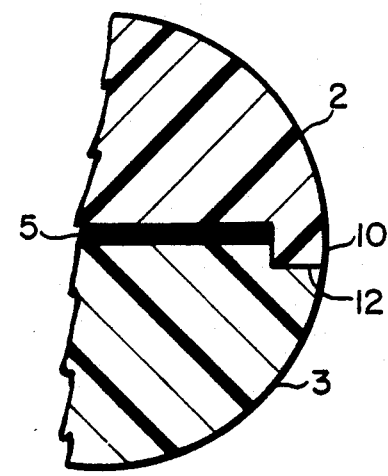
FIG. 5 is an enlarged, partial section through composite rod structure taken along line 5—5 in FIG. 3.

In the preferred embodiment, the spacings 5 and 6 are determined by holding the components in a fixture when the bonding process is done. Another method for setting the spacing between the two annular segments is to form the parts with a raised land along one component side and a groove on the mating component side as shown in the enlarged, partial cross-sectional view of FIG. 5. Each annular segment then has the identical cross section of the mating segment. The land 10 and groove 12 on both diametral extremes set the spacing between annular segments; coaxial centering of the annular segments about the central rod then requires only a centering fixture.

In discussing the salient features of the invention circular geometry was used for convenience. It will be apparent to those skilled in the art that non-circular perimeters of the components are equally viable shapes to accomplish the fabrication of a composite rod from which lens blanks with two or more colors can be cut.

As pointed out above, the haptics should not be colored with dyes or other soluble colorants because of the danger that the coloring material will diffuse outward from the haptics over the period of time the implant is in the eye. The selection of an insoluble coloring material is limited because of the requirements of governmental health agencies. One such approved material is copper phthalocyanine in the beta crystal phase in concentrations up to 0.1%, which is quite adequate for proper coloring. The impregnation process can entail mixing the copper phthalocyanine in particulate form of approximately one micron size with polymerized PMMA of suitable molecular weight distribution. The mixture is intimately comingled by a high-energy mixer such as an attritor or ball mill, until homogeneous, resulting in a master batch pigment. This pigment is then added to the liquid monomer MMA, followed by the addition of more polymer to increase the viscosity and to reduce shrinkage during polymerization. When this process is followed, the particulates will be uniformly dispersed throughout the volume of the resulting colored PMMA. The size of the coloring particles is determined so that when viewed under a 20-power microscope, the haptic will appear to be uniformly colored and not exhibit objectionable optical granularity. The method for coloring the haptic material as described here is only one of several methods known to those skilled in the art, any of which may be used with the method of this invention. Colored haptic material made in the manner described here will have identical physical properties with the lens itself and thus will not introduce mechanical strains at the interface between the lens and the haptic.

Figure 1B:
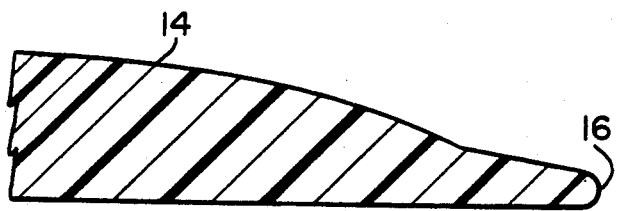
FIG. 1B is a partial cross section of the one-piece intraocular lens along line 1B—1B of FIG. 1A.
Figure 2A:
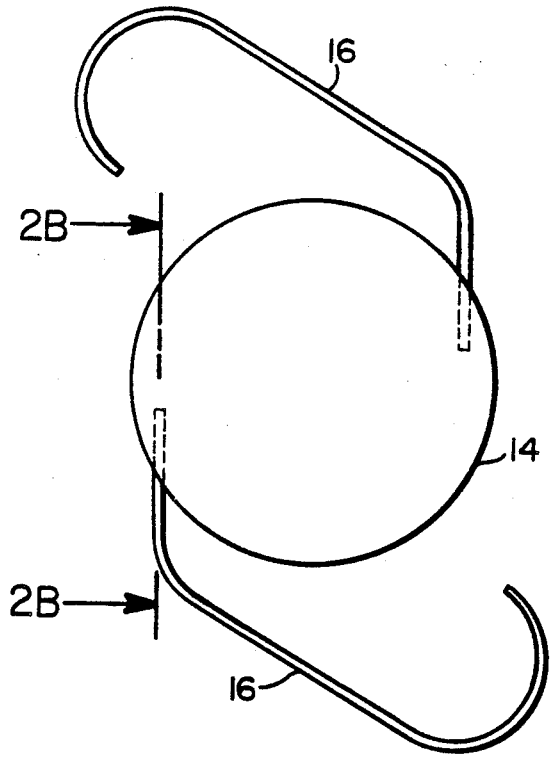
FIG. 2A is a plan view of a three-piece intracular lens assembly of the prior art showing the lens and attached filamentary haptics.
Figure 2B:
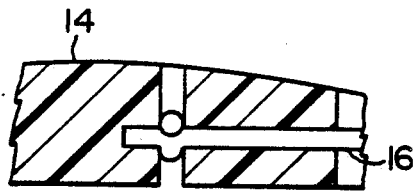
FIG. 2B is a partial cross section of the three piece intraocular lens assembly along line 2B—2B of FIG. 2A.
Figure 6A:
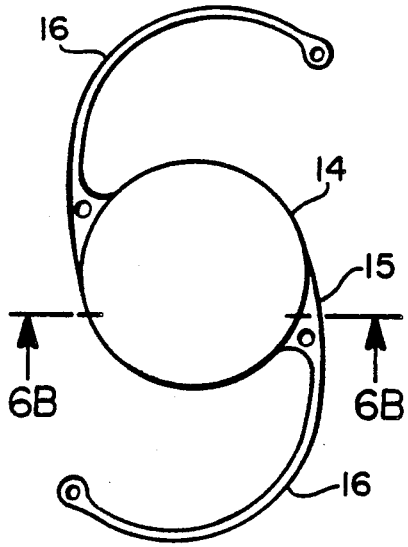
FIG. 6A is a plan view of a monolithic lens and haptic assembly machined from the slice of composite rod.
Figure 6B:
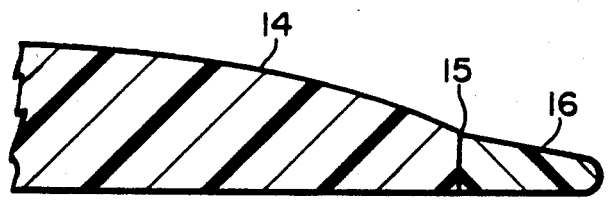
FIG. 6B is a partial cross section of the monolithic lens taken along line 6B—6B of FIG. 6A.

Once the colored haptic material has physical characteristics matching those of the lens, it is only necessary to devise a polymerizable liquid bonding medium to fill the spacings 5 and 6 in FIG. 1. This liquid medium, when hardened, will bond to each surface and will have the same physical characteristics as the lens and the haptic, forming a monolithic assembly with no discontinuities in physical properties throughout the volume. The liquid medium can be made in a manner analogous to the making of the colored haptic material. Starting with the liquid monomer MMA, adding optional colorants, a polymerization initiator, and PMMA of suitable molecular weight distribution to increase viscosity to the desired level and reduce shrinkage during bonding, a liquid bonding medium for filling the spacings is obtained. The roughened surfaces of the mating parts increase the surface area presented to the liquid and facilitate intimate bonding of the pieces. Polymerization may be initiated, facilitated, accelerated or brought to greater conversion, that is to say, higher molecular weight or lower residual monomer content, by multiple energy inputs. These energy inputs include ultraviolet light, thermal energy, ultrasonic energy and ionizing radiation. After polymerization, the joints between the haptic material and the lens are essentially the same material as the haptics and lens; the two-color assembly is a solid block of material with no discontinuities in physical properties. If desired, the preparation of the liquid medium and/or the bonding operation can take place under vacuum to insure that no bubbles are trapped at the interface. Once the solid block of material has been fabricated, it is a simple matter to cut off slices of the rod to form blanks from which monolithic intraocular lenses with colored haptics can be machined. The monolithic lens of FIGS. 1A and 1B made according to the method of this invention is shown in FIGS. 6A and 6B. In the latter case, however, the haptics 16 are colored. The enlarged partial cross section of FIG. 6B shows the clear lens material 14 and the colored haptic 16 joined at the line 15 where the bond between the two pieces is made. Note that when formed in this configuration, the bond occurs at the point of maximum cross-sectional area of the haptic, although other configurations could be used if desired.

What is claimed is:

1. A method for making an intraocular lens with integral colored haptics comprising the steps of
    fabricating an optically transparent polymeric rod with a cross section large enough for an intraocular lens and with a length sufficient for forming a plurality of lenses;
    fabricating at least two polymeric segments closely matching the contour of a mating surface of said transparent polymeric rod to form segments thereon and with a cross section large enough for the forming of haptics, said segments having at least on color;
    applying a bonding agent between the rod and segments;
    positioning said segments about said rod;
    allowing the bonding agent to bond the segments to the rod thereby forming a multi-colored, monolithic cylinder;
    slicing the cylinder into discs to form blanks from which intraocular lenses can be machined; and
    machining the blanks to form lenses with colored haptics integral with the body of the lens.

2. A method for making an intraocular lens with integral colored haptics as in claim 1 wherein
    said optically transparent polymeric rod is of circular cross section; and
    said segments have a length nominally that of the rod, are of circular cross section, and each subtends an angle of 180 degrees.

3. A method for making an intraocular lens with integral colored haptics as in claim 1 wherein
    said segments are made of stretched acrylic.

4. A method for making an intraocular lens with integral colored haptics comprising the step
    fabricating an optically transparent polymeric rod with a cross section large enough for an intraocular lens and with a length sufficient for forming a plurality of lenses;
    fabricating at least two polymeric, colored, annular sectors closely matching the contour of and spaced a small distance from the surface of said transparent polymeric rod to form annular segments with a cross section large enough for the forming of haptics, said polymeric, colored, annular segments having at least one color and having a length nominally that of the transparent polymeric rod; mixing a polymerizable liquid medium for bonding said optically transparent polymeric rod to said polymeric, colored, annular sectors, said polymerizable liquid, when hardened, having mechanical properties matching the optically transparent polymeric rod and the polymeric, colored, annular segments;
    positioning said polymeric, colored, annular segments symmetrically about said transparent polymeric rod;
    filling the space between the mating surfaces of said optically transparent polymeric rod and said polymeric, colored, annular segments and the spaces between the mating surfaces of the polymeric, colored, annular segments with said polymerizable liquid medium;
    allowing the polymerizable liquid medium to harden, thereby forming a multi-colored, monolithic composite cylinder;
    slicing the multi-colored, monolithic composite cylinder into discs to form blanks from which lenses can be machined; and
    machining the blanks to form lenses with colored haptics integral with the body of the lens.

5. A method for making an intraocular lens with integral colored haptics a in claim 4 wherein
    said optically transparent polymeric rod is of circular cross section; and
    said polymeric, colored, annular segments are nominally identical, of circular cross section, and subtend an angle of 180 degrees.

6. A method for making an intraocular lens with integral colored haptics as in claim 4 wherein
    said positioning of said polymeric, colored, annular sectors with respect to each other and to said optically transparent polymeric rod is accomplished by means of holding fixtures.

7. A method for making an intraocular lens with integral colored haptics as in claim 4 wherein
    said positioning of said polymeric, colored, annular sectors with respect to each other is accomplished by a self-fixturing means formed on said polymeric, colored, annular segments and with respect to said optically transparent polymeric rod is accomplished by a holding fixture.

8. A method for making an intraocular lens with integral colored haptics as in claim 4 wherein
    said polymeric, colored, annular segments are made of stretched PMMA.

9. A method for making an intraocular lens with integral colored haptics as in claim 4 wherein
    said optically transparent polymeric rod is made of material with selectively tailored wavelength transmission characteristics.

10. A method for making an intraocular lens with integral colored haptics as in claim 4 wherein
    said optically transparent polymeric rod is made of material with radially varying refractive index.

11. A method for making an intraocular lens with integral colored haptics as in claim 4 wherein
    said optically transparent polymeric rod is chosen from a class of optically active materials which include photochromic and optically non-linear materials for control of light transmission through the lens.

* * * * *